United States Patent [19]
Calebaugh

[11] Patent Number: 5,341,802
[45] Date of Patent: Aug. 30, 1994

[54] ENDOTRACHEAL TUBE STABILIZING DEVICE

[76] Inventor: John D. Calebaugh, 203 Via Serena, Rancho Santa Margarita, Calif. 92688

[21] Appl. No.: 3,092

[22] Filed: Jan. 11, 1993

[51] Int. Cl.$^5$ .......................................... A61M 16/00
[52] U.S. Cl. ...................... 128/207.17; 128/DIG. 15; 128/DIG. 26
[58] Field of Search ..................... 128/200.26, 207.14, 128/207.15, 207.17, 912, DIG. 26, DIG. 15

[56] References Cited

U.S. PATENT DOCUMENTS

| | | | |
|---|---|---|---|
| 4,326,515 | 4/1982 | Shaffer et al. | 128/DIG. 26 |
| 4,331,144 | 5/1982 | Wapner | 128/DIG. 26 |
| 4,392,857 | 7/1983 | Beran | 128/207.17 |
| 4,592,351 | 6/1986 | Smith et al. | 128/207.17 |
| 4,622,034 | 11/1986 | Shattuck | 128/DIG. 26 |
| 4,774,943 | 10/1988 | Yu | 128/DIG. 26 |
| 4,844,061 | 7/1989 | Carroll | 128/DIG. 26 |
| 5,038,778 | 8/1991 | Lott | 128/207.17 |
| 5,042,477 | 8/1991 | Lewis | 128/207.17 |
| 5,076,269 | 12/1991 | Austin | 128/DIG. 26 |

Primary Examiner—Edgar S. Burr
Assistant Examiner—Aaron J. Lewis
Attorney, Agent, or Firm—Knobbe, Martens, Olson & Bear

[57] ABSTRACT

A releasable endotracheal tube stabilizing device having a retaining unit for adjustably securing the endotracheal tube, an adhesive head assembly of medical grade foam tape with slits in a centrally located integral attachment member for receiving and positioning the retaining unit, two D-shaped rings which are secured to lateral ends of the head assembly, and a stretchable neckband detachably connected to the D-rings that encircles the patient's neck for stabilization. The retaining unit is operative to secure or release the endotracheal tube while the neckband and head assembly remains in place. The neckband includes hook and loop surfaces to permit removal of a cervical collar and reassembly of the stabilization device without dislodging the endotracheal tube.

12 Claims, 3 Drawing Sheets

ENDOTRACHEAL TUBE STABILIZING DEVICE

FIELD OF THE INVENTION

This invention relates to medical instruments, and specifically to an improved apparatus and method for stabilizing and securing an endotracheal tube.

BACKGROUND OF THE INVENTION

In the field of respiratory care, an endotracheal tube may be placed directly into the trachea, or airway, for ventilation via a life support system. Currently there are a number of ways and products on the market for stabilizing an endotracheal tube. The problems of stabilizing an endotracheal tube with the use of tape have been well-documented in the past. In the field of respiratory care, when patients are being ventilated through a mechanical ventilator, warm, humidified gasses are used to prevent the airway from drying, and to prevent the body from giving up moisture in order to humidify this gas. Consequently, these gasses also warm the endotracheal tube, which reduces the adhesiveness and securing ability of tape. This increases the possibility of inadvertent extubation and dislodgement of the tube, a potentially life-threatening situation. Not only does the heat and humidity decrease the adhesiveness, but this, in concert with oral secretions, greatly increases the chances of inadvertent dislodgement occurring.

In light of today's hospital environment and the advent of HIV in patient blood and secretions, the ideal endotracheal tube stabilizing device is one that reduces the amount of exposure time involved in stabilizing the tube. It is common practice for respiratory care practitioners to wear latex protective gloves to prevent the spread of hospital-acquired infection, but the use of gloves has proven difficult as the gloves stick to the tape. The ideal endotracheal tube stabilizing device therefore would be easy to install and remove while wearing gloves, would reduce unnecessary exposure to the clinician, and would prevent nosocomial infection.

Specific to the trauma setting, patients often come into the hospital with head injury, facial trauma and profuse bleeding. In these cases, stabilizing the tube can be nearly impossible because the blood fully saturates the tape as it is being applied around the face and endotracheal tube. Also, every trauma patient who has a suspected neck injury, arrives at the hospital wearing a cervical collar to prevent further injury. In the event of a decrease in the patient's neurological status, the physician will electively decide to intubate the patient as a safety precaution as a C.T. scan is performed to rule out bleeding within the brain cavity. The endotracheal tube is thus secured using tape around the cervical collar. If the endotracheal tube is placed too far down into the trachea, the tube will have to be retracted for proper ventilation, and the entire process of securing the tube repeated. After an X-ray examination, if the results are negative for injury, and after removal of the X-ray equipment, the cervical collar will be removed, requiring the tape to be removed, and the entire stabilization process repeated to adequately secure the tube.

The ideal endotracheal tube stabilizing device would be for single-patient use, disposable, packaged clean, contain low manufacturing costs, and would be a charged item for the hospital.

As mentioned previously, there are a number of medical devices on the market today for stabilization of the endotracheal tube. Most encompass some type of a glue to secure the tube. While in most instances the outward appearance of these look sturdy, it is not until the patient is turned from side to side or lifted for morning X-ray does the tube become dislodged.

SUMMARY OF THE INVENTION

It is therefore the object of this invention to provide a new and improved endotracheal tube stabilizing device of such a design that when an endotracheal tube is inserted either through the mouth or the nose, the tube can be secured with sufficient firmness to prevent slippage in either direction, regardless of the accumulation of body fluids around the tube.

Another object of this invention is to provide a new and improved stabilizing device that is easily secured after proper placement of the tube into the trachea, and is easily releasable and resecurable in the event the tube is not in the proper placement after confirmation by chest X-ray.

Another object of this invention is to provide a stabilizing device that will accommodate all sizes of endotracheal tubes for ventilation by anesthetic and general life-support systems.

Another object of this invention is to provide a stabilizing device that is hypoallergenic in nature for those instances when it is necessary to provide ventilation for extended periods of time, preventing allergic dermatitis to the facial area.

Still another object of this invention is to provide a stabilizing device that utilizes a semi-stretchable neckband is that when used in conjunction with a neurologic patient who has increased intercranial pressure from trauma, the stabilizing device provides enough support to prevent dislodgement of the tube but does not restrict the blood flow to the brain, endangering the patient further.

Another object of this invention is to provide an endotracheal tube stabilizing device which provides ease in removal of the entire unit in the event of elective extubation by the physician, or ease of removal and restabilization in the event the cervical collar is removed after clearance by lateral neck X-ray in the absence of cervical fractures.

A variety of structures may be employed, and not all features described herein are required to realize the advantages of this invention. With these objects in view, this invention consists in construction, arrangement, and concert with the combination of various parts of the stabilizing device, whereby the objects contemplated are attained as hereafter set forth and pointed out in the claims and accompanying drawings.

In accordance with a preferred embodiment, a releasable endotracheal tube stabilizing device includes a one-piece retaining post with an elongated tab extending from the lateral end of the retaining post, the tab containing grooves for retention when secured. The retaining post has a resilient detent tab which interacts with the grooves on the elongated tab in a ratchet fashion so that the tab may be pulled through a central slot in the retaining post and held in a secure position. An end of the tab opposite the retaining post is pre-inserted through a central punched attachment of a head assembly constructed of adhesive medical grade foam tape, and through the central slot in the post. The lateral aspects of the head assembly are attached to D-shaped rings. One end of a stretchable Velcro loop and hook assembly is pre-inserted through one of the D-shaped rings and fastened back upon itself.

When utilized, the adhesive backing of the head assembly is peeled, the central retaining unit placed over the head of the endotracheal tube down to a desired marking on the tube, and the retaining unit secured to the tube by pulling the pre-inserted elongated tab through the retaining post, the inserted position of the tab being maintained by the resilient detent tab. The remainder of the medical grade foam tape is placed on the patient's lip for oral intubation or over the bridge of the nose for nasotracheal intubation. The lateral end of the head assembly housing the D-shaped ring and neckband assembly is placed underneath the patient's neck. The terminal end of the neckband having a hook portion is passed through the unattached D-shaped ring and secured back against the stretchable loop portion. The advantage of this system is that when secured, the mechanism that holds the endotracheal tube secure is the adhesive from the head assembly and lateral wall pressure when the central retaining unit is securely fastened. In preferred form, the lateral wall pressure does not distort the inside diameter of the endotracheal tube, but merely holds with enough firmness to adequately secure the tube.

To perform an adjustment to the retaining unit in the event of improper placement into the trachea, the resilient detent tab is pulled in a direction away from the elongated tab and is held in this open position while the elongated tab is pushed back through the retaining post, thus increasing the circumference of the retaining unit. When proper placement is achieved, the detent tab is released and the elongated tab pulled back through the retaining post to the desired tension around the endotracheal tube.

Adjustments to the neckband are accomplished by simply releasing either side of the hook and loop assembly and threading back through the D-shaped ring. The advantage of this configuration is that the neckband can be released to remove a cervical collar without having to remove the head assembly that is holding the endotracheal tube stabilized.

DETAILED DESCRIPTION OF THE PREFERRED EMBODIMENTS

Figure 1:
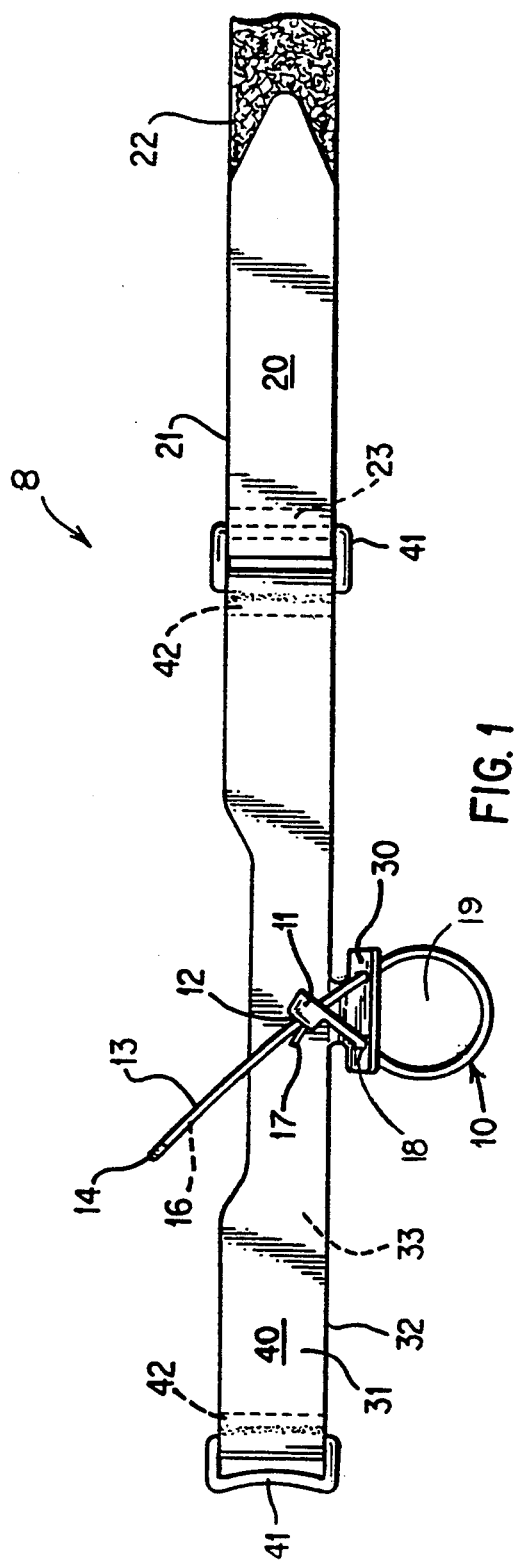
FIG. 1 is a front elevational view of the endotracheal tube stabilizing device of the present invention.
Figure 4:
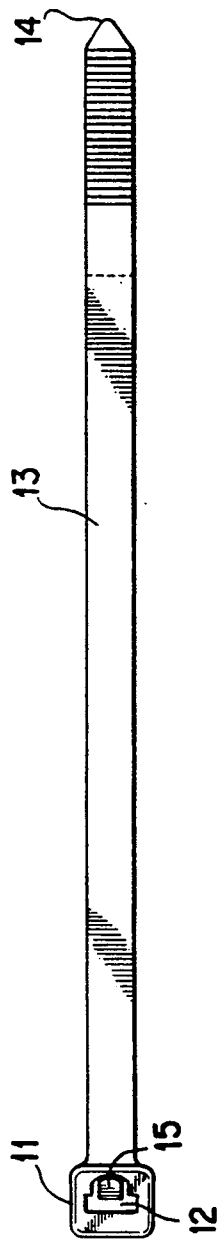
FIG. 4 is a top plan view of a retaining unit.
Figure 5:
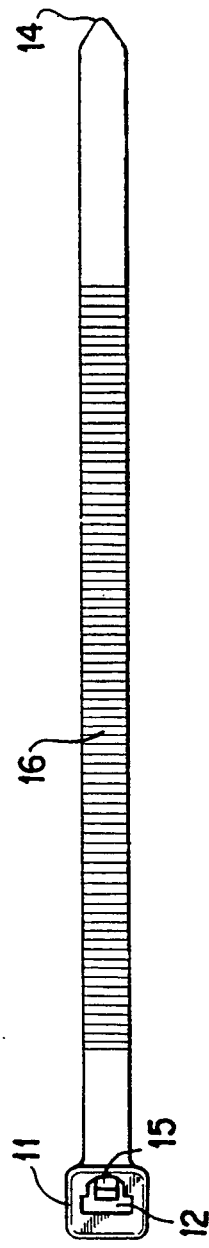
FIG. 5 is a bottom plan view of the retaining unit of FIG. 4.

With reference to FIG. 1, an endotracheal tube stabilizing device 8 comprises a retaining unit 10, a neckband unit 20, a central punched attachment 30, and a head assembly 40. The retaining unit 10, also shown in FIGS. 4 and 5, includes an elongated tab 13 having a tapered end 14, the tapered end being passed through slits 18 in the central punched attachment 30 before being inserted through a central slot 12 in a retaining post 11. The retaining post 11 includes an integral resilient detent tooth 15 and release latch 17 which engages with a series of grooves 16 on one side of the elongated tab 13. The retaining unit 10 thus defines a variable sized loop or aperture 19 for receiving and exerting lateral wall pressure on an endotracheal tube (not shown).

Figure 1A:
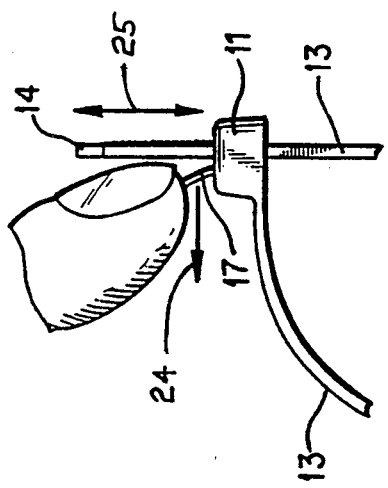
FIG. 1A is a detailed view of an adjustment mechanism of a retaining unit of the tube stabilizing device.

FIG. 1A shows the adjustment procedure for varying the size of the aperture 19. By manually actuating the release latch 17, the resilient detent tooth 15 is biased away from the elongated tab 13 in the direction of arrow 24 out of engagement with the grooves 16. The elongated tab 13 may then be slid in the direction of double arrow 25 with respect to the retaining post 11. In the view of FIG. 1A, sliding the elongated tab 13 up will decrease the size of tube-receiving aperture 19, while sliding the tab in the opposite direction will increase the size of the aperture.

Figure 2:
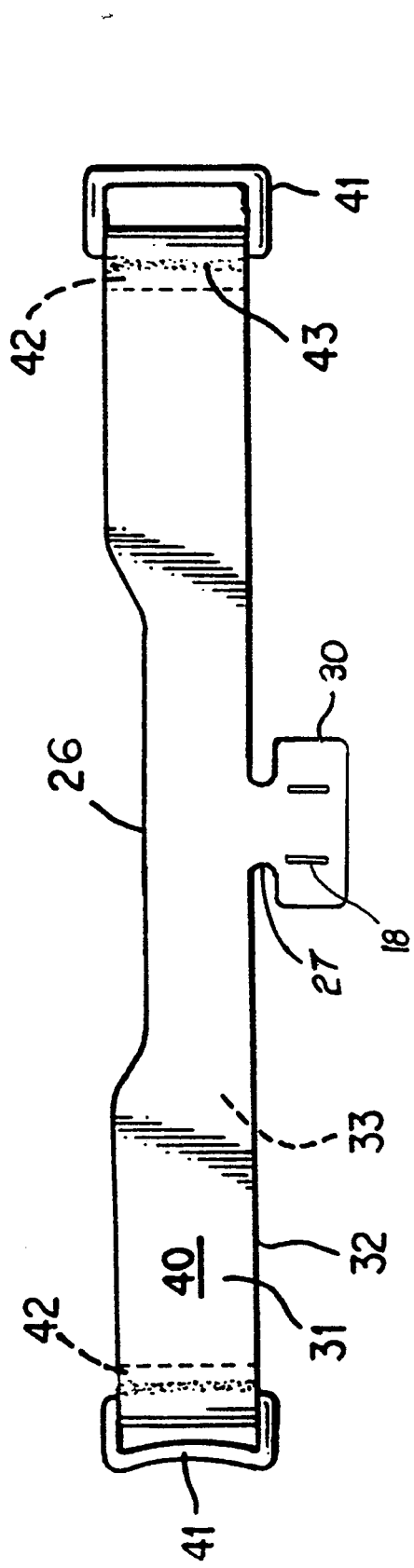
FIG. 2 is a front elevational view of a head assembly.
Figure 3:
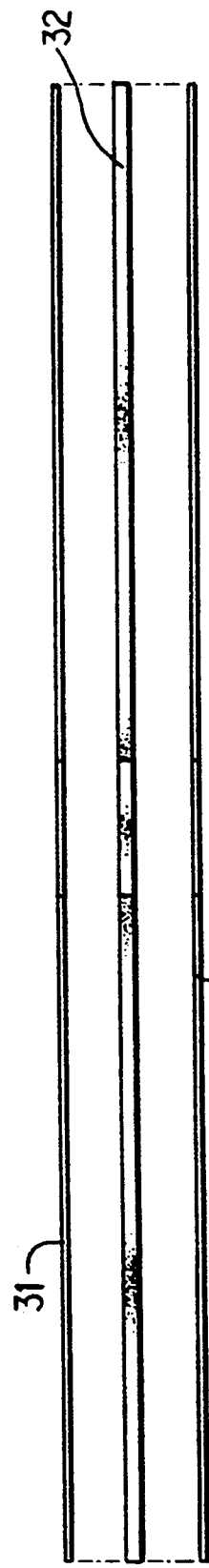
FIG. 3 is an exploded view of the layered construction of the head assembly of FIG. 2.

FIG. 2 illustrates the head assembly 40 having a centrally extending integral punched attachment 30 and a pair of D-shaped rings 41 attached at either end. As depicted in FIG. 3, the head assembly 40 has a layered construction with an outer non-absorbent pressure sensitive material 31 bonded to an inner layer of medical grade foam 32 and an adhesive peel backing 33 on the underside. The head assembly 40 generally comprises an elongated rectangular strip of material having an upper indent 26. The adhesive surface on the rear side of the central foam layer 32 allows the head assembly 40 to be adhered in place on the face of the patient. The central punched attachment 30 comprises a generally rectangular body attached to the lower edge of the head assembly 40 by a neck portion 27. The narrowed neck portion 27 provides a pivot point for the main body of the central punched attachment 30, as seen in FIG. 1.

The combined attachment 30 and punched slits 18 provide a locating means through which the retaining unit 10 is pre-inserted to position and attach the endotracheal tube with respect to the head assembly 40. In this respect, the endotracheal tube is inserted into either the mouth or nasal passage of the patient, and the retaining unit 10, attached to the head assembly 40, tightened thereupon. Due to the adherence of the head assembly 40, the central punched attachment 30 and retaining unit 10 are positioned centrally on the face of the patient to receive and stabilize the endotracheal tube.

Figure 6:
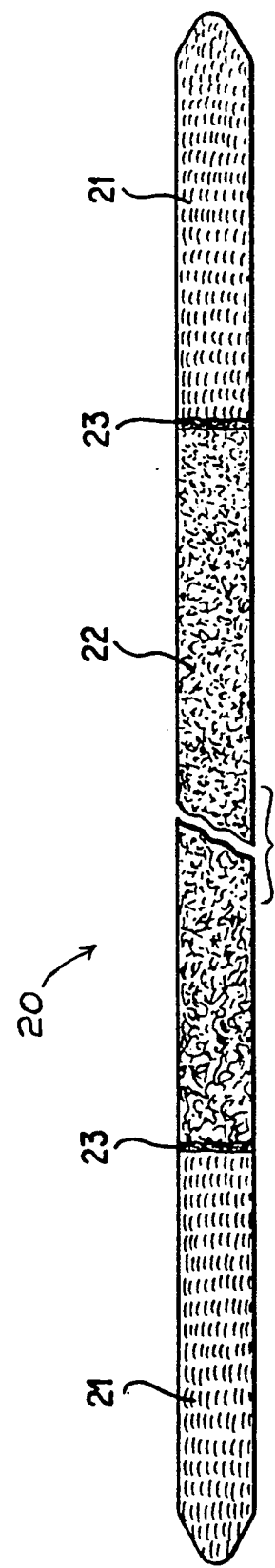
FIG. 6 is a front elevational view of a preferred neckband of the present invention.

As shown in FIGS. 1 and 2, the lateral ends of the flexible head assembly 40 are inserted through the D-shaped rings 41 and bonded back upon themselves utilizing a self-adhesive foam seam 42. The neckband 20 is shown in FIG. 6 and generally comprises a central portion 22 having a surface of loop material and two lateral portions 21 having surfaces of hook material, the central and lateral portions preferably attached by an embossed seam 23. In one embodiment, the seam 23 is ultrasonically embossed.

As seen in FIG. 1, one end of the neckband assembly 20 is inserted through one of the lateral D-shaped rings 41 so that the loop portion 21 can be folded back upon the hook portion 22 to connect the neckband with the head assembly 40. After placement of the head assembly 40 and retaining unit 10 onto the patient's face and around the endotracheal tube, respectively, the second end of the neckband assembly 20 may be passed behind the patient's head and connected to the unattached D-shaped ring 41. The central portion 22 of the neckband assembly 20 is constructed of a stretchable material which provides support for the head assembly 40 in its tube stabilizing capacity yet does not exert undue pressure on the patient's head, possibly restricting blood flow. Advantageously, the neckband 20 does not apply tension directly to the endotracheal tube but rather to the lateral D-shaped rings 41 of the adhesively secured head assembly 40.

To install the stabilizing device 8, after proper endotracheal or nasotracheal tube placement, the adhesive peel backing 33 is removed from the medical grade foam 32, revealing the non-allergic adhesive surface underneath. The retaining unit 10, after insertion through the slits 18 in the punched attachment 30, is placed over the endotracheal tube down to a proper identification marker on the shaft of the endotracheal tube, whereupon the head assembly 40 is adhered to the face of the patient. The foam construction of the head assembly 40 allows it to conform to the shape of the patient's face. The underlayer of adhesive securely holds the head assembly 40 in place, while the narrow neck portion 27 provides a pivot point for the central punched attachment 30. The diameter of the tube receiving aperture 19 is adjusted by pulling the elongated tab 13 through the retaining post 11 so that the endotracheal tube is held in place by both lateral wall pressure of the tab and also from contact with the adhesive surface on the underside of the central punched attachment 30. The combination of being tightly held by the retaining unit 10 and being in adhesive contact with the central punched attachment 30 securely holds the endotracheal tube in place with respect to the stabilization device 8. Moreover, the operation of repositioning the tube may be facilitated by the adhesive contact between the punched attachment 30 and the tube.

As mentioned above, the head assembly 40 is placed over the patient's upper lip in oral endotracheal tube placement, and over the bridge of the nose for nasotracheal tube placement. The adhesive undersurface of the head assembly 40 holds the stabilizing device 8 secure while the neckband assembly 20 is being attached. In the event the patient has a suspected neck injury, and has a cervical collar in place, once an X-ray examination has indicated there is no injury, one or both of the hook and loop connections of the neckband 20 may be removed to allow the removal of the cervical collar. After removal, the hook portion 21 is simply passed through the D-shaped ring 41 and folded back to be attached to the loop portion 22. In the event of improper placement of the endotracheal tube into the airway, the resilient detent tooth 15 is pulled away from the elongated tab 13 and held open, while the elongated tab is pushed through the central slot 12 of the retaining post 11 to adjust the size of the aperture 19 and allow repositioning of the endotracheal tube. After the tube is retracted or advanced within the trachea, the retaining unit 10 is then secured as previously described at the proper identification marker on the endotracheal tube. Thus, it can be seen that the present invention provides a dual security stabilization device. If the endotracheal tube must be repositioned, the entire stabilizing device 8, secured by the neckband assembly 20, remains in place, while the retaining unit 10 is adjusted. If, on the other hand, a cervical collar must be removed, or the neckband 20 removed for other reasons, the head assembly 40 remains adhesively secured to the patient's face, and thus, the endotracheal tube remains stabilized.

I claim:

1. A device for stabilizing an endotracheal tube in a patient, comprising:
   a flexible head assembly defined by a substantially flat strip having an adhesive backing surface for adhering to a patient's face and having opposed lateral ends secured to rings, said head assembly including a centrally extending attachment portion defining a pair of slits;
   a tube retaining unit formed by a thin elongated tab having a tapered end and a releasable lock on an end opposite said tapered end, said tube retaining unit being positioned centrally with respect to said head assembly by inserting said tapered end of said tube retaining unit through said pair of slits in said attachment portion of said head assembly, said retaining unit forming an adjustable loop by inserting said tapered end through a slot in said lock, said loop being adjustable to firmly hold and retain said endotracheal tube in a substantially fixed position with respect to said head assembly; and
   a neckband having hook and loop attachment surfaces for connecting to said rings, said neckband passing around the patient's head adding additional stabilization of the endotracheal tube.

2. The device of claim 1, wherein said retaining unit comprises an integral detent tooth in said lock and said tab includes a plurality of tooth-engaging grooves, said tooth normally being biased toward said grooves and having a manual release latch for adjusting said loop.

3. The device of claim 1 wherein said attachment portion comprises a generally rectangular body and said slits are formed in said body parallel to each other and perpendicular to a line defined between said lateral ends of said head assembly, said body integrally connected to said head assembly by a neck portion, said neck portion providing a pivot point for said body.

4. The device of claim 1 wherein said attachment portion further comprises an adhesive backing surface and wherein said tube contacts said attachment portion and is held in place by adhesion in conjunction with lateral wall pressure exerted by said retaining unit.

5. The device of claim 1, wherein said neckband includes at least one portion of stretchable fabric to allow for slight tensioning of said stabilizing device without exerting undue pressure to restrict blood flow in the patient's head.

6. The device of claim 1, wherein said neckband is sized large enough to surround a cervical collar around a patient's head.

7. The device of claim 1, wherein all of the components of said stabilizing device are constructed of material compatible with Magnetic Resonance Imaging signals.

8. The device of claim 1, wherein all of the components of said stabilizing device are constructed of material compatible with X-rays.

9. The device of claim 1, wherein said head assembly is defined by an elongated strip having a top layer of pressure-sensitive non-absorbent material, an inner layer of medical grade foam having an adhesive lower surface, and a lower layer of adhesive peel backing.

10. The device of claim 9, wherein said adhesive on said foam layer is hypoallergenic.

11. A method of stabilizing an endotracheal tube that has been inserted in a patient, comprising the steps of:
   providing an endotracheal tube;
   providing a grooved elongated tab having a free end and a detent lock opposite said free end; providing a head assembly having opposed ends and a central attachment portion with slits therethrough; providing an adhesive backing on said head assembly and attaching a pair of rings to said opposed ends;

threading the free end of the elongated tab through the slits and through the detent lock thereby forming a retaining loop; and engaging the endotracheal tube with said loop;

pressing said head assembly to the patient's face, said head assembly thus being secured to the patient's face with the centrally positioned retaining loop engaging said tube;

providing a neckband having opposed ends; and connecting at least one of the opposed ends of the neckband to at least one of the rings; passing the other of said opposed ends of the neckband around the head of a patient to assist the head assembly in stabilizing the endotracheal tube.

12. The method of claim 11, further comprising the following steps after the engaging step:

adjusting the size of said retaining loop by manually releasing a detent tooth of said detent lock from engagement with a groove in said elongated tab and sliding said tab with respect to said lock;

repositioning said endotracheal tube with respect to said retaining loop; and re-engaging said endotracheal tube with said retaining loop.

* * * * *